(12) United States Patent
Hampstead et al.

(10) Patent No.: US 11,865,328 B2
(45) Date of Patent: Jan. 9, 2024

(54) NEUROPSYCHOLOGICAL AND NEUROLOGICAL REHABILITATION HEADGEAR DEVICE

(71) Applicant: THE REGENTS OF THE UNIVERSITY OF MICHIGAN, Ann Arbor, MI (US)

(72) Inventors: Benjamin Hampstead, Ann Arbor, MI (US); Allena Holzworth, Ann Arbor, MI (US); Kevin Kramer, Ann Arbor, MI (US); Alexander Rothmann, Ann Arbor, MI (US); Shannon Ryan, Ann Arbor, MI (US)

(73) Assignees: THE REGENTS OF THE UNIVERSITY OF MICHIGAN, Ann Arbor, MI (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 17/188,437

(22) Filed: Mar. 1, 2021

(65) Prior Publication Data
US 2021/0268266 A1    Sep. 2, 2021

Related U.S. Application Data

(60) Provisional application No. 62/983,978, filed on Mar. 2, 2020.

(51) Int. Cl.
*A61N 1/04* (2006.01)
*A61N 1/20* (2006.01)
*A61B 5/291* (2021.01)

(52) U.S. Cl.
CPC ............ *A61N 1/0456* (2013.01); *A61B 5/291* (2021.01); *A61N 1/0476* (2013.01); *A61N 1/0484* (2013.01); *A61N 1/20* (2013.01)

(58) Field of Classification Search
CPC .. A61N 1/0456; A61N 1/0476; A61N 1/0484; A61N 1/0526; A61N 1/0529
See application file for complete search history.

(56) References Cited

U.S. PATENT DOCUMENTS 7,551,952 B2    6/2009   Gevins et al.
9,031,631 B2 *  5/2015   Tong .................... A61B 5/6803
                                                            600/545

(Continued)

OTHER PUBLICATIONS

"Personalized TMS helmets for quick and reliable TMS administration outside of a laboratory setting." Brain Stimulation 13 (2020) 551-553.

*Primary Examiner* — Alyssa M Alter
(74) *Attorney, Agent, or Firm* — Harness, Dickey & Pierce, P.L.C.

(57) ABSTRACT

A customizable headgear assembly for neuropsychological and neurological treatment, monitoring, or testing of a patient. The headgear assembly comprising a structural frame having a plurality of anatomical landmark tabs each individually configured to be located upon an anatomical landmark of a patient's head. The structural frame having first and second portions releasably coupled to enable the first and second portions to be at least partially separated for placement and removal from the patient's head. A plurality of electrode holders being operable coupled to the structural frame each configured to locate an electrode upon a predetermined neurological position of the patient.

18 Claims, 18 Drawing Sheets

(56) References Cited

U.S. PATENT DOCUMENTS

| | | |
|---|---|---|
| 9,440,063 B2 | 9/2016 | Ho et al. |
| 9,440,070 B2 | 9/2016 | Goldwasser et al. |
| 9,854,988 B2 | 1/2018 | Oakley et al. |
| 2007/0106170 A1 | 5/2007 | Dunseath et al. |
| 2015/0119689 A1* | 4/2015 | Pascual-Leone ...... A61N 2/006 600/407 |
| 2016/0302683 A1 | 10/2016 | Lawrence et al. |

* cited by examiner

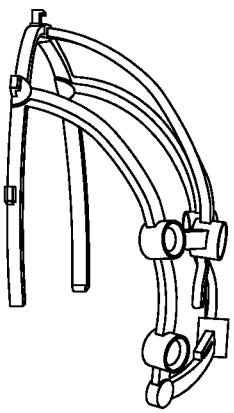
FIG. 39
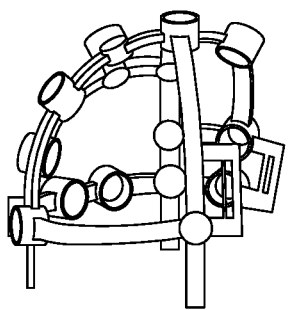 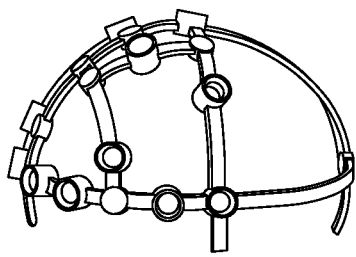 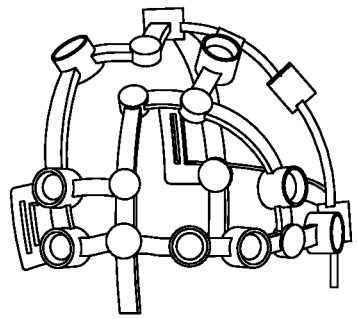
FIG. 40   FIG. 41   FIG. 42
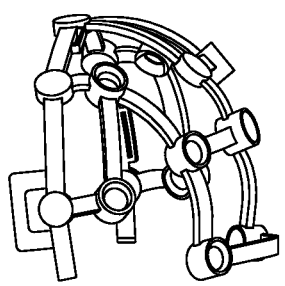 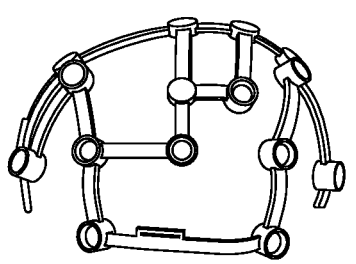 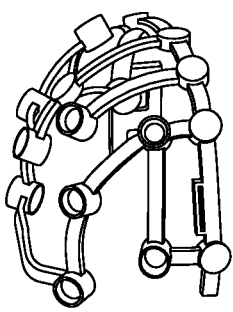
FIG. 43   FIG. 44   FIG. 45

Please Follow Instructions to Highlight Respective Landmarks or 3D Model

Please Highlight Nasion

Back    Continue

Please Follow Instructions to Highlight Respective Landmarks or 3D Model

Please Highlight Inion

Back    Continue

NEUROPSYCHOLOGICAL AND NEUROLOGICAL REHABILITATION HEADGEAR DEVICE

CROSS-REFERENCE TO RELATED APPLICATIONS

This application claims the benefit of U.S. Provisional Application No. 62/983,978, filed on Mar. 2, 2020. The entire disclosure of the above application is incorporated herein by reference.

FIELD

The present disclosure relates to neuropsychological and neurological treatment and/or monitoring and, more particularly, relates to a device that facilitates rapid, accurate, and convenient delivery of non-invasive brain stimulation, such as transcranial direct current stimulation.

BACKGROUND AND SUMMARY

This section provides background information related to the present disclosure which is not necessarily prior art. This section provides a general summary of the disclosure and is not a comprehensive disclosure of its full scope or all of its features.

Currently, there are 5.7 million Americans living with Alzheimer's disease. This number is greater when considering those with all causes of dementia. It is projected this number will grow to 14 million by 2050. Currently, there is no treatment to stop or slow the progression of the disease; medications provide, at best, modest symptomatic relief.

However, according to the principles of the present teachings, a device is provided that facilitates accurate, rapid, and convenient delivery of non-invasive brain stimulation; the goal of which is to allow at-home and remotely monitored treatment for cognitive deficits arising from neurologic injury and disease.

Transcranial direct current stimulation (tDCS) is a form of non-invasive brain stimulation that is being investigated as a non-pharmacologic method of cognitive enhancement. In traditional pad-based tDCS, weak electrical current passes between two electrodes—an anode and a cathode—placed on the scalp at various positions using the accepted 10-20 (or 10-10) system, as will be described herein. The electrical current flows from the anode to the cathode.

Alternatively, "high definition" tDCS (HD-tDCS) uses multiple, smaller electrodes positioned in a wide range of configurations (also called a montage). The use of "HD-tDCS" refers to any multi-electrode approach and is not limited a specific device or manufacturer. HD-tDCS can comprise one or more anodes and cathodes, which are placed to optimize current flow and/or focality. It should be understood that accurate electrode placement is critical for ensuring that stimulation reaches (or is optimized at) specific brain regions. Inaccurate placement of electrodes may not only mitigate effects but could result in potentially harmful unintended consequences.

Pad-based tDCS is comparatively easy to administer and pre-measured head straps have been developed to promote in-home use. However, patients (or their caregivers) must accurately place the large rubber electrodes inside of sponges, saturate the sponges with saline solution (too little saline can mitigate effects and lead to skin burns, while too much may drip and shunt current away from the intended areas), and then place them on the head using a one-size fits all approach (e.g., plastic head straps that come in only a few sizes and are not individually tailored). This conventional approach can be prone to error, especially in the hands of cognitively impaired patients.

Likewise, HD-tDCS is similar in difficulty to pad-based tDCS in that it requires the user to be able to measure multiple points on the head, fill the electrode holder with gel, and place the electrode within the holder. This can again be difficult to employ in a home environment, especially in the hands of cognitively impaired patients. Thus, there is currently no method that permits HD-tDCS to be simply and reliably performed at home.

According to the principles of the present teachings, a device and method of creating and using the device for HD-tDCS and other applications is provided. In some embodiments, the method of creating the device results in a rigid (i.e., non-pliable) and customized (i.e., individually tailored) device (i.e., headgear) that ensures reliable and standardized placement of electrodes for use in HD-tDCS. It should be understood, however, that in some embodiments the device of the present teachings can be used in a wide variety of applications, such as, but not limited to, separate and/or concurrent HD-tDCS, EEG, fNIRS, and other types of neuromodulation or measurement of neurophysiology.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 22-45 illustrate perspective views of exemplary structural frames for varying sizes of patients and/or various applications and/or techniques according to the principles of the present teachings, wherein:

FIGS. 22-24 illustrate perspective views, particularly a left anterior view, a middle left side view, and a right posterior view, of an exemplary structural frame having electrode holder locations (10/10 system) at Fp1, F1, F5, F9, C5.

FIGS. 25-27 illustrate perspective views, particularly a left anterior view, a middle left side view, and a right posterior view, of an exemplary structural frame having electrode holder locations (10/10 system) at Fpz, AFz, AF3, AF7, F1, F5, F9, FC1, FT7.

FIGS. 28-30 illustrate perspective views, particularly a left anterior view, a middle left side view, and a right posterior view, of an exemplary structural frame having electrode holder locations (10/10 system) at Cz, C3, C4, CP1, CP2, P9, P10, T7, T8, O1, O2, Oz.

FIGS. 31-33 illustrate perspective views, particularly a left anterior view, a middle left side view, and a right posterior view, of an exemplary structural frame having electrode holder locations (10/5 system) at FPz, F7, AFFS, C5, C3, FT9, F9, FFCS, FCz, Fz.

FIGS. 34-39 illustrate perspective views, particularly a left anterior view, a middle left side view, and a right posterior view for the left half and left anterior view, a middle right side view, and a right posterior view for the right half, of an exemplary 2-piece structural frame having electrode holder locations (10/10 system) at F7, F8, T7, T8, P7, P8, EX5, EX6, EX13, EX14.

FIGS. 40-42 illustrate perspective views, particularly a left anterior view, a middle right side view, and a right posterior view, of an exemplary structural frame having electrode holder locations (10/10 system) at Cz, C4, CP1, CP2, T8, TP8, P6, P03, P08, 01, 02.

FIGS. 43-45 illustrate perspective views, particularly a left anterior view, a middle left side view, and a right posterior view, of an exemplary structural frame having electrode holder locations (10/10 system) at Fp1, F1, F5, F9, C5, CP3, P1, P5, P9, 01.

Corresponding reference numerals indicate corresponding parts throughout the several views of the drawings.

DETAILED DESCRIPTION

Figure 1:
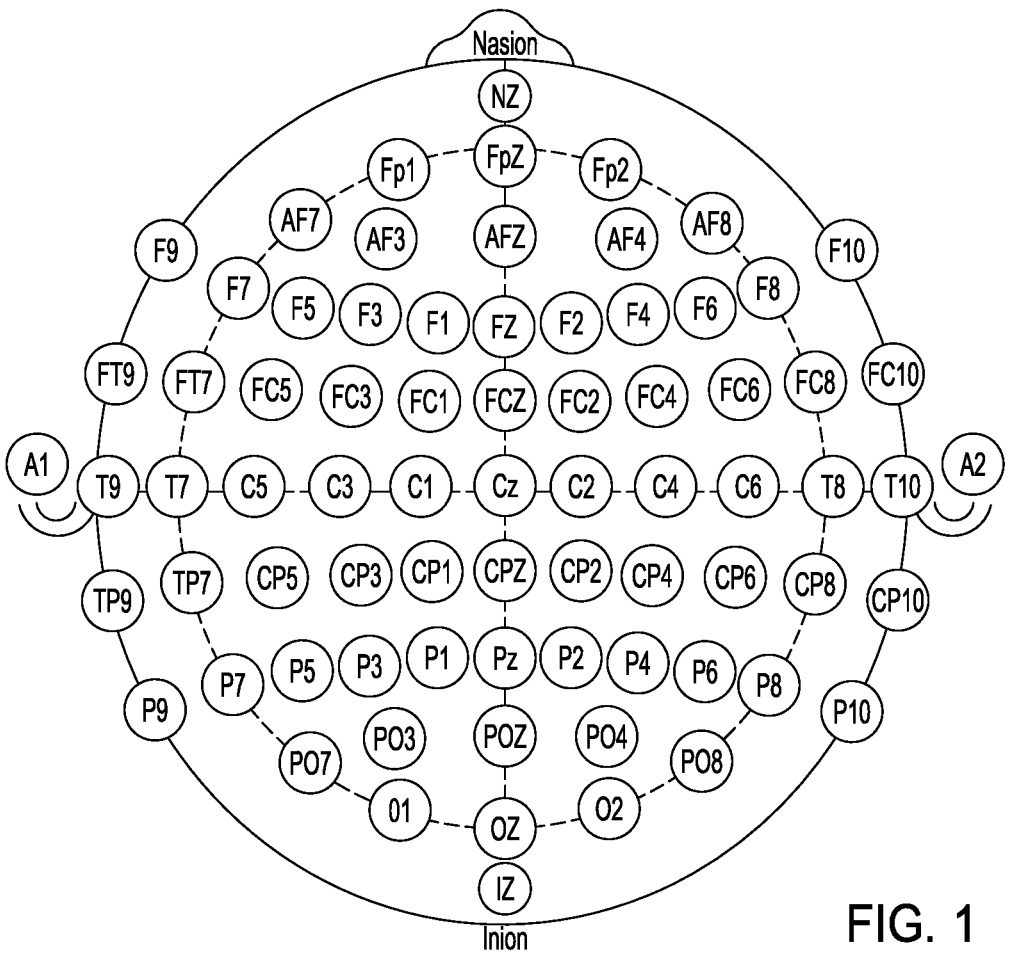
FIG. 1 illustrates a 10/10 electrode placement system including electrode labels, such as nasion, inion, and the preauricular points as A1 and A2.

Example embodiments will now be described more fully with reference to the accompanying drawings.

Example embodiments are provided so that this disclosure will be thorough and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Briefly, by way of background, it is believed that a discussion of existing electrode placement techniques would be beneficial to an understanding of the device and method of the present teachings.

Existing Electrode Placement Approach

Currently, electrode placement on a patient's head is based on the accepted 10/10 (or 10/20 or 10/5) System of the American Clinical Neurophysiology Society (FIG. 1), which is used in electroencephalogram (EEG), functional near infrared spectroscopy (fNIRS), and related techniques. This system relies on measurements of distance between set "landmarks" on the head. These landmarks include the nasion (bridge of nose), inion (bump on back of skull), and the preauricular points (notches in front of the ears). The distance of each location is based on a proportion of the distance between these landmarks and the overall head circumference.

Figure 2:
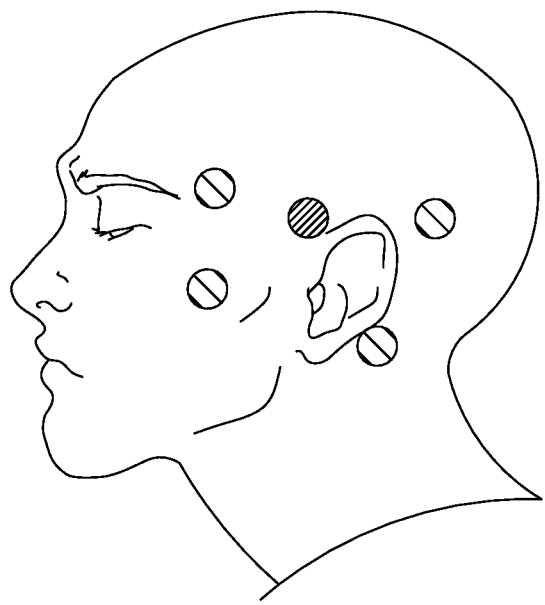
FIG. 2 illustrates an exemplary bi-temporal electrode montage for patients who have mild cognitive impairment (MCI) and dementia.

Conventionally, accurate measurement and electrode placement requires the user to be well trained, which limits translation given a general paucity of resources necessary to train patients and their caregivers/families. Moreover, the measurement and placement process can be highly time consuming as it is not uncommon to require more than 40 minutes to place 5 to 10 electrodes, as seen in FIG. 2, even by a trained individual.

Figure 3A:
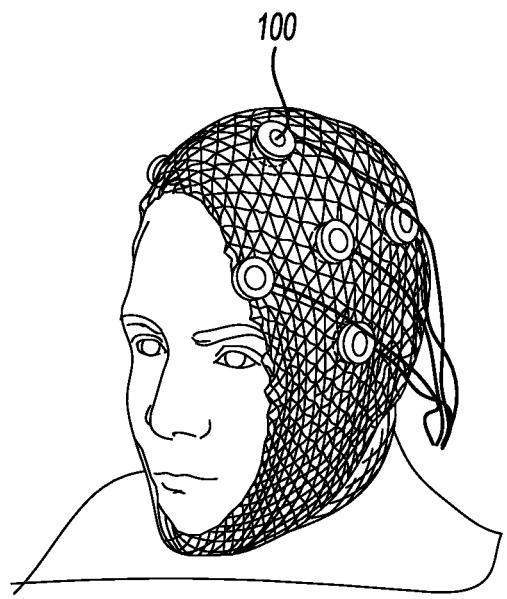
FIGS. 3A-3C are examples of conventional head nets or caps used for electrode placement.
Figure 3B:
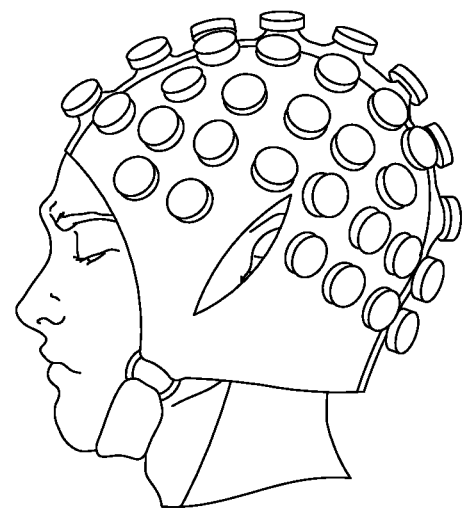
Figure 3C:
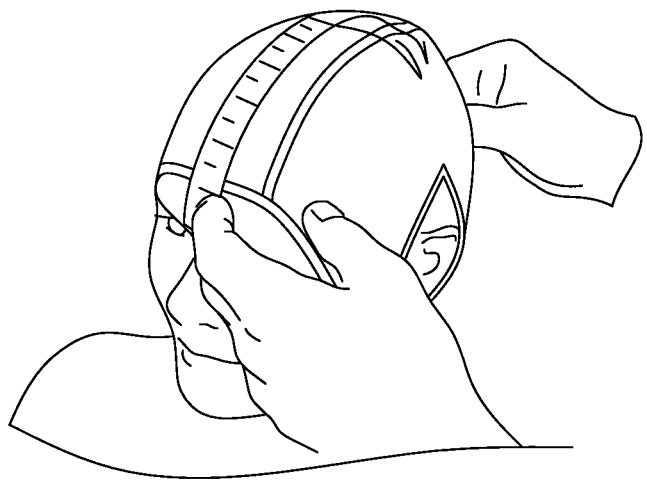

Conventionally, once sites have been identified and marked (e.g., using a marker), the user must affix an electrode holder against the head using some form of cap. As illustrated in FIGS. 3A-3C, existing electrode holders can fit into either flexible head mesh or a neoprene cap (similar to a swimmer's cap with holes in it). A predetermined amount of electrode gel is then placed in the holder before the electrode is placed into the holder (and in contact with the gel), and a cap positioned to ensure the electrode does not become dislodged. Following stimulation, the process is reversed and electrodes and their holders (and cap, if possible) must be washed. The elastic head netting is discarded, leading to waste and ultimately increasing cost. This entire process must be repeated each session.

Generally, all current solutions utilize forms of elastic material that employ a "one size fits all" approach. However, the flexibility of the material can lead to marked discrepancies in electrode placement, even when landmarks are appropriately used. In fact, it has been found that conventional practices can lead to electrode placement discrepancies of up to 20 mm or more; an error rate that is unacceptable for neuro rehabilitative purposes (and/or measurement of neurophysiology).

Thus, there is a need for a simple, repeatable, accurate, and cost-effective device and method to facilitate HD-tDCS, neuromodulation, and/or neurophysiologic monitoring, such as EEG or fNIRS. The device according to the principles of the present teachings overcomes the disadvantages of the prior art and performs as well as or significantly better than conventional systems and methods. More particularly, as described herein, the headgear and methods of the present teachings provides an individually tailored device that can accurately place one or more electrodes in various combinations of locations upon a patient's head according to the 10/10 (or 10/5+) System. Moreover, the headgear of the present teachings is easily compatible with other types of electrodes (e.g., pads, EEG, fNIRS) and can be, in some embodiments, individually tailored using MRI-based localization of specific brain structures of an individual patient. Therefore, the headgear of the present teachings is the only truly customizable product available, with equal applications across forms of neuromodulation (e.g., tDCS, transcranial alternating current stimulation (tACS), transcranial random noise stimulation (tRNS), forms of light stimulation) and neurophysiological measurement (e.g., EEG, fNIRS).

A customizable, affordable, and reusable method and headgear device for providing HD-tDCS, as disclosed in some aspects of the teachings herein, holds remarkable potential to increase participant/patient flow due to time savings, save costs, and enable in-home (or remotely monitored) use. Such in-home treatment would reduce patient burden (e.g., transportation, time in the laboratory/clinic), increase the dosage (e.g., number of sessions provided), enhance long-term compliance and, possibly, improve quality of life. The reduction in cost, both opportunity cost and monetary value would benefit the patient, the clinician/researcher, and society (e.g., potential for healthcare savings).

Design of Headgear and Components

According to the principles of the present teachings, a headgear assembly 10 is provided that is individually tailored for accurately placing one or more electrodes 100 in various combinations of locations upon a patient's head according to the 10/10 (or 10/5+) System or other desired treatment or monitoring plan. It should be appreciated that in some embodiments, placement of electrodes 100 can be individually tailored using MRI-based localization of specific brain structures of an individual patient (e.g., using neuronavigation approaches to identify the region of the head overlying a particular brain structure and then using that location as the electrode site—even if it does not conform to the 10/10 System). Once MRI-based localization of specific brain structures of the individual patient is identified, and optionally, once a desired treatment or monitoring plan has been selected, software of the present teachings can automatically design a 3D model of the headgear with the electrode holders placed at selected locations of the individual's head and support bars added to connect the electrode holders together, and then render a final model for review. It should be understood that in some embodiments the localization of specific brain structures can be obtained via a CT or MRI scan and integrated with a 3D scan of the head using readily available tools, such as but not limited to smartphone or tablet cameras and/or devices/peripherals (e.g., iPad with 3D camera attachment).

In some embodiments, headgear assembly 10 is compatible with a wide variety of electrodes 100 (e.g., pads, EEG, fNIRS). Headgear assembly 10 is highly customizable and has utility in a wide variety of applications, such as but not limited to neuromodulation (e.g., tDCS, transcranial alternating current stimulation (tACS), transcranial random noise stimulation (tRNS), forms of light stimulation) and neurophysiological measurement (e.g., EEG, fNIRS).

Structural Frame

Figure 4:
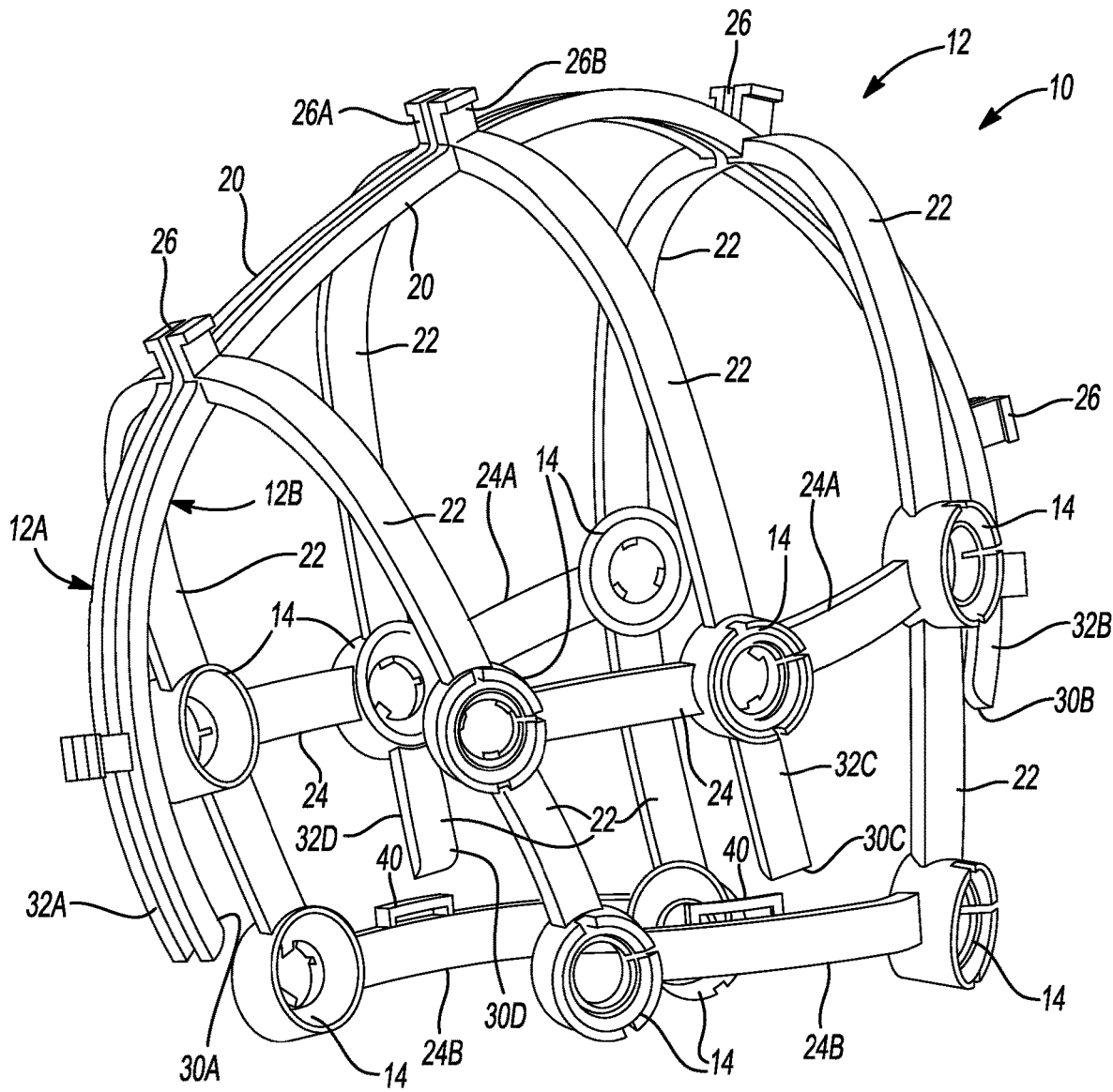
FIG. 4 illustrates a perspective view of the headgear assembly according to the principles of the present teachings.

With particular reference to FIG. 4, in some embodiments, headgear assembly 10 (or headgear, cap, helmet, or the like) can comprise a structural frame 12. In some embodiments, structural frame 12 is generally rigid and, preferably, customized and fabricated for an individual patient. However, it should be understood that in some embodiments, structural frame 12 can be constructed for a similarly-configured class of patients having corresponding cranial landmark positions. In some embodiments, structural frame 12 can be a single, integral frame network depending on electrode locations and cranial construction. However, it is anticipated that in some embodiments, structural frame 12 can comprise two or more structural sections 12A, 12B ( . . . 12n) that are joined together.

In some embodiments, structural frame 12 is a rigid structure that ensures repeatable placement on a patient's head, provides rigidity to the overall system, and provides reliable and repeatable placement of electrodes 100 on a patient's head. In some embodiments, structural frame 12 (and entirety or portions of headgear assembly 10) can be constructed in accordance with the principles outlined herein and/or via 3D printing or other rapid manufacturing methods. Moreover, structural frame 12 (and entirety or portions of headgear assembly 10) can be constructed of a singular material or a plurality of materials located at various positions to increase/decrease/optimize rigidity, flexibility, electrical properties, and/or other parameters.

Spine/Rib Members/Support Members

As illustrated in FIG. 4, structural frame 12 can comprise two structural sections 12A, 12B each having a central spine section 20 generally configured to be placed along a medial line generally extending along the top of the cranium. As will be described herein, the central spine section 20 of each of the structural sections 12A, 12B can be configured to be selectively abutted, selectively joined, selectively nested, or otherwise arranged adjacent to the other central spine section 20. In some embodiments, structural frame 12 can comprise one or a plurality of crossbar rib members 22 generally extending orthogonally downward from each of the central spine sections 20 and generally following a cranial contour of the patient. In some embodiments, structural frame 12 can further comprise one or a plurality of interconnecting support members 24 extending between the plurality of crossbar rib members 22. It should be recognized that the present configuration is particularly well suited for use with patients with hair as hair can be easily passed through the openings extending between the plurality of crossbar rib members 22 and the plurality of interconnecting support members 24 without adversely affecting the location and contact of the electrodes. In contrast, conventional designs can often experience further displacement and/or improper positioning due to trapping of hair under the cap.

In some embodiments, by way of non-limiting example, central spine section 20, crossbar rib members 22, and interconnecting support members 24 can be approximately 1 cm in width, 0.5 cm in thickness, and define rounded corners and/or edges to prevent injury during handling and usage.

As is illustrated in FIG. 4, in some embodiments, interconnecting support members 24 can interconnect adjacent crossbar rib members 22 (see 24A) or can interconnect nonadjacent rib members 22 (see 24B). In some embodiments, interconnecting support members 24 can be used to provide increased structural integrity and support to structural frame 12. In some embodiments, interconnecting support members 24 can be used to join and/or support one or more electrode holders 14, which in turn provides proper placement of electrode 100 at predetermined locations of a patient's head and further provides proper relative placement of each electrode from the others. This is particularly important to ensure that application of a stimulus or signal, or monitoring of signals, is not negatively influenced by improper absolute or relative electrode placement. In some embodiments, each electrode holder 14 can be formed along one or more of crossbar rib members 22 and, in some embodiments, along interconnecting support members 24 to provide reliable support for electrodes 100 and reduced stress concentrations within structural frame 12. It should be understood that although each electrode holder 14 can be coupled to one of crossbar rib member 22 or interconnecting support member 24, in some embodiments, each electrode holder 14 (as illustrated) is joined on two, three, or even four sides to one or more crossbar rib member 22 and/or interconnecting support member 24. In this way, electrode holder 14 is reliably coupled to structural frame 12 to ensure proper absolute placement of electrodes 100 on a patient's head and proper relative placement of each electrode 100.

Landmark Tabs

With reference to FIG. 4, in some embodiments, structural frame 12 of headgear assembly 10 comprises at least one, but preferably two, three, four, or more landmark tabs 30 that provide predetermined/predefined reference points to ensure proper placement of headgear assembly 10 upon a patient's head. In some embodiments, landmark tabs 30 are associated with specific anatomical locations on the patient. For example, landmark tab 30A can comprise a front distal end 32A of one or more central spine sections 20 that is placed at the nasion of the patient. Similarly, landmark tab 30B can comprise a rear distal end 32B of one or more central spine sections 20 that is placed at the inion of the patient. Finally, in some embodiments, landmark tabs 30C, 30D can comprise left and right distal ends 32C, 32D of a corresponding crossbar rib member 22 that is placed at the left and right preauricular points of the patient. Accordingly, each landmark tab 30 lays or hovers directly over the anatomical references to allow proper location of electrode holders 14 and, thus, electrodes 100. In some embodiments, it has been found that employing at least two to three reference points and associated landmark tabs 30 results in proper placement of assembly 10 upon a patient's head. When structural frame 12 is configured to have two or more structural sections 12A, 12B, then each of these structural sections can comprise one, two, or ideally three landmark tabs 30 to ensure proper and consistent placement of the headgear. Additional, or potentially fewer, reference points could be used in the future as necessary on an individualized basis to ensure optimal placement/fit.

Connector Posts

Figure 5:
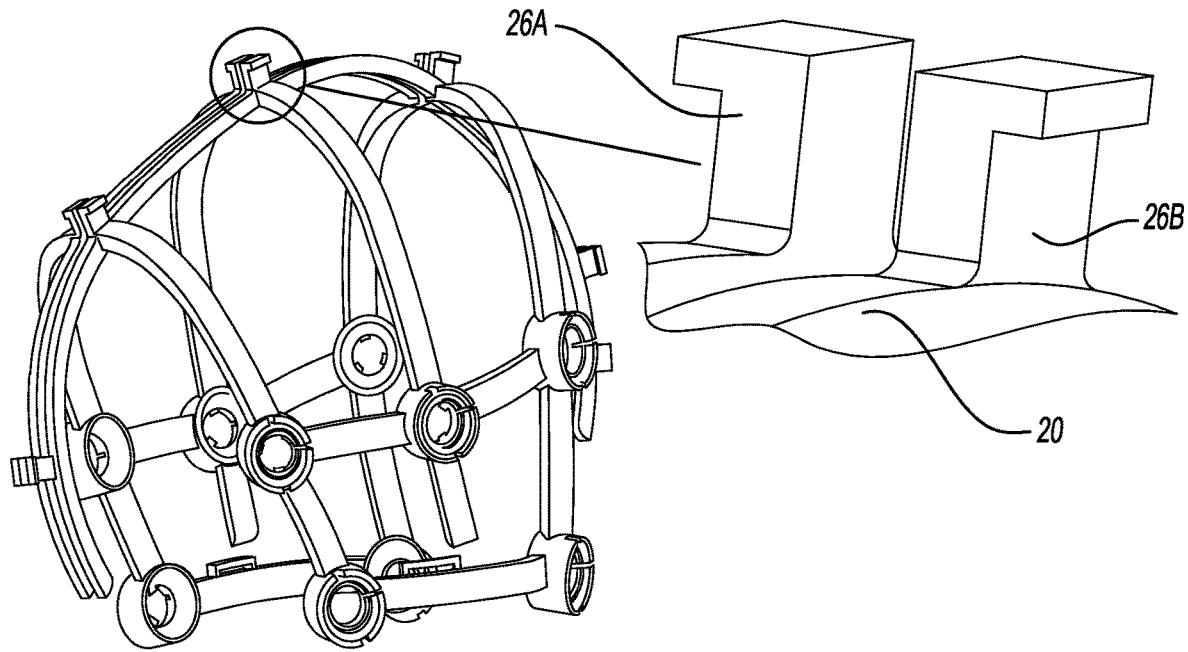
FIG. 5 illustrates an enlarged perspective view of connector posts according to the principles of the present teachings.

With reference to FIGS. 4 and 5, in some embodiments employing two or more structural sections 12A, 12B of structural frame 12, structural sections 12A, 12B can be joined or otherwise coupled to permit convenient placement and removal of headgear assembly 10 on a patient. In this regard, structural frame 12 can be finely constructed to follow the contours of the patient's cranial landscape without regard to placement and removal discomfort concerns. In some embodiments, structural sections 12A, 12B can be partially tethered, joined, hinged, or otherwise coupled to permit a clamshell-type opening operation. However, it should be recognized that a wide variety of connector posts configurations are within the scope of the present teachings, including but not limited to snap-fit, press-fit, friction fit, and other joining combinations or techniques. Although a wide variety of coupling systems is anticipated, in some embodiments, a plurality of paired connector posts 26 can be disposed along central spine sections 20 such that when structural sections 12A, 12B are joined, each of the paired connector posts 26A, 26B are adjacently positioned and/or sufficiently aligned to permit coupling. In some embodiments, coupling can be completed using a coupling method, device, and/or system. In some embodiments, the coupling method, device, and/or system can comprise a retaining member or device, such as but not limited to a clip, a clamp, an elastic member (i.e. rubber band), a mechanical interconnection (i.e. releasable hinge), and the like to ensure repeatable and reliable connection of structural sections 12A, 12B. It has been found that coupling methods, devices, and/or systems that provide some flexure (i.e. rubber bands) and/or provides compliancy may be more comfortable for a patient. That is, this arrangement still maintains proper placement of the electrodes on the patient, but provides increased comfort compared to fully fused structural frames. It should be understood that this connection method should be simple to permit a cognitively impaired patient or caregiver to actuate or install.

By way of non-limiting example, in some embodiment, the base of each connector post 26 is 0.4 cm×0.8 cm and approximately 0.6 cm tall, with a top that is 0.6 cm×0.8 cm and 0.2 cm tall. A single rubber band (or similar) is wrapped around the bases of two connector posts 26. As illustrated in FIG. 5, an upper or distal portion of each connector post 26 can comprise an enlarged portion for retaining the rubber band or clip. However, it should be understood that the size, shape, and configuration of connector posts 26 could vary.

Figure 6:
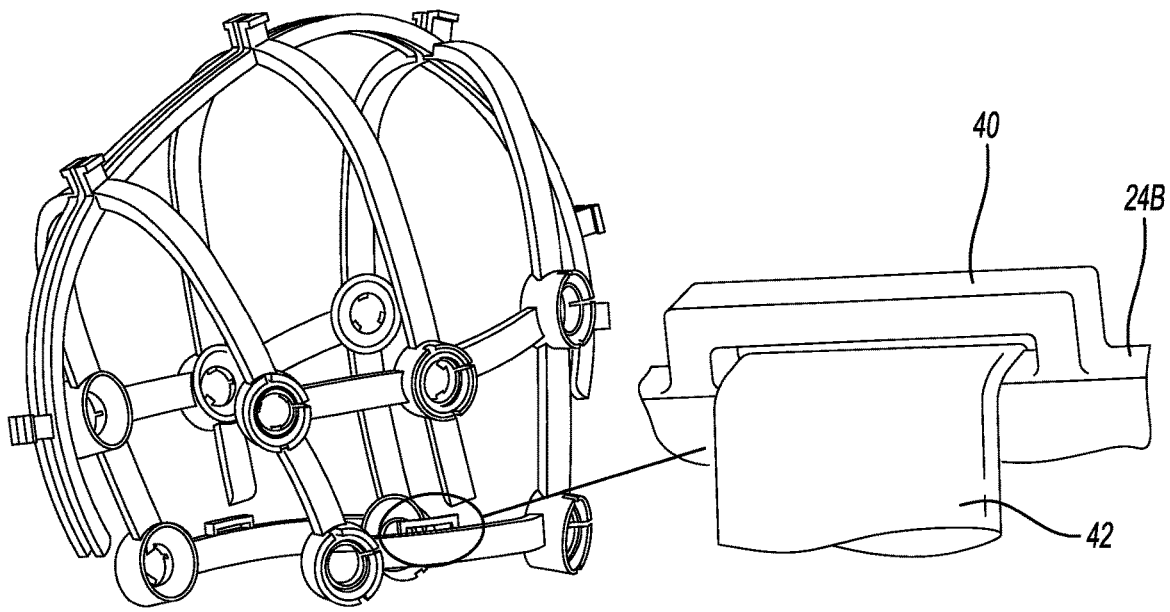
FIG. 6 illustrates an enlarged perspective view of strap loops according to the principles of the present teachings.

With reference to FIGS. 4 and 6, in some embodiments, structural frame 12 can comprise one or more strap retainer or loop member 40 for coupling with a strap member 42. In some embodiments, loop member 40 can comprise a slot 44 formed in or along structural frame 12, such as along interconnecting support member 24B. Loop members 40 enable headgear assembly 10 to be secured to the head of the patient to prevent shifting of headgear assembly 10 and electrodes 100 during use. Strap 42 can be threaded through the loop to provide secure attachment along the chin of the patient, over the top of the head, around the front, back, and/or side of the head.

Electrode Holder/Electrode Cup

Figure 7:
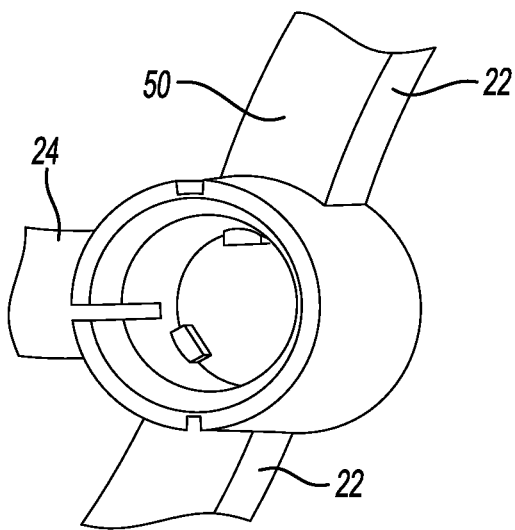
FIG. 7 illustrates an enlarged perspective view of an electrode label according to the principles of the present teachings.

In some embodiments, as illustrated in FIGS. 4 and 7, headgear assembly 10 can comprise a plurality of electrode holders 14 for capturing and/or retaining a corresponding electrode 100 at a desired location on the head and improving contact with the head/scalp of the patient. In some embodiments, the headgear assembly 10 comprises 1, 2, 3, 4, 5, 6, 7, 8, 9, 10, 11, 12, 13, 14, 15, 16, 17, 18, 19, 20, or more electrode holders 14. In some embodiments, electrode holders 14 can be configured to hold and/or retain any one of a number of types of electrodes for various electrode testing, treatment, and/or monitoring systems directly within electrode holder 14 or within a suitable electrode cup 60. Electrode holders 14 and/or electrode cup 60 can be sized and shaped to retain electrodes of various size, shape, and/or function, such a dry or wet electrodes. Additionally, electrode holders 14 and/or electrode cup 60 can be configured to enable separate or concurrent use of EEG, fNIRS, and other methods to evaluate, monitor, or alter neurophysiology.

In some embodiments, each electrode holder 14 and/or electrode cup 60 can be filled with a conductive material (e.g. gel, saline, electrode paste) to enable the delivery of tES and/or measurement of neurophysiological activity (e.g., EEG, fNIRS). The consistent size of electrode holder 14 and/or electrode cup 60 ensures a consistent and well-measured amount of conductive material, thereby standardizing procedures from one session to the next thereby optimizes tolerability and safety. In some embodiments, electrode holder 14 can be configured to enable use of common fNIRS optodes and EEG electrodes.

Figure 8:
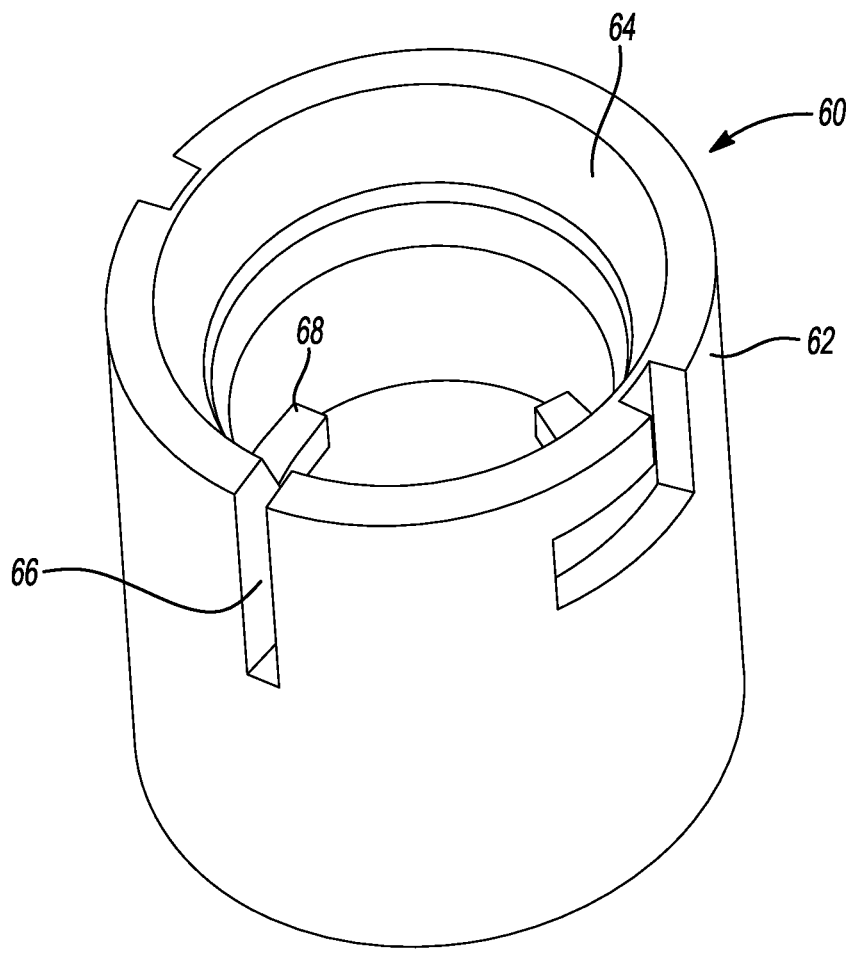
FIG. 8 illustrates an enlarged perspective view of an electrode cup according to the principles of the present teachings.

With particular reference to FIG. 8, the electrode cup 60 is illustrated. It should be understood that the structure described herein in connection with electrode cup 60 can be equally applicable to electrode holder 14 being formed integrally with structural frame 12. In this way, electrode cup 60 would be unnecessary. However, in some embodiments, electrode holder 14 can be universally shaped to accept an electrode cup 60 therein to enable electrodes of differing size and/or application to be used in a single headgear assembly 10. In such embodiments, the electrode holder 14 may be configured to matingly accept, and securably but reversibly couple to, the electrode cup 60 via a snap fit, friction fit, interlocking or threaded twist fit, press fit, or any other suitable connection means. In the interest of brevity, it should be understood that description relating to the structure and/or function of electrode cup 60 is equally applicable to electrode holder 14 in some embodiments.

With continued reference to FIG. 8, in some embodiments, electrode cup 60 can comprise an exterior shape 62 that can be received within a corresponding volume of electrode holder 14. In some embodiments, as described herein, electrode cup 60 can be integrally formed with structural frame 12. Electrode cup 60 can comprise an electrode cavity 64 sized to receive electrode 100. A wire of electrode 100 can extend through a wire slot 66 formed in a sidewall of electrode cup 60. One or more electrode tabs 68 can be formed within electrode cavity 64 to position and/or hold electrode 100 within electrode cavity 64 to provide proper positioning of electrode 100 and further provide, in some embodiments, a standoff distance from electrode cavity 64 to permit electrode gel to surround electrode 100.

Figure 9:
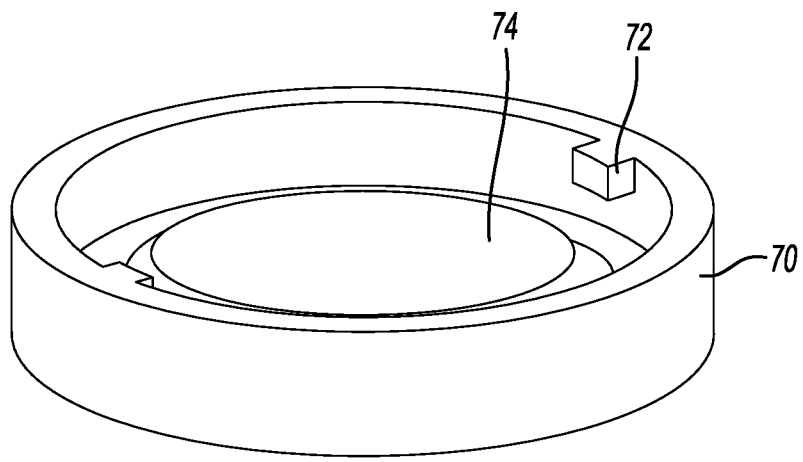
FIG. 9 illustrates an enlarged perspective view of an electrode cap according to the principles of the present teachings.
Figure 10:
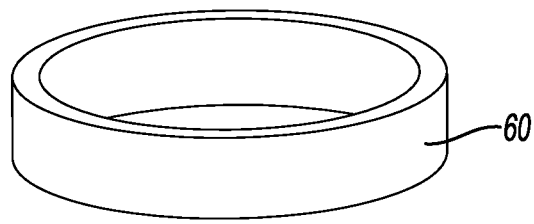
FIGS. 10-21 illustrate perspective views of electrode cups of varying sizes and angles according to the principles of the present teachings.
Figure 11:
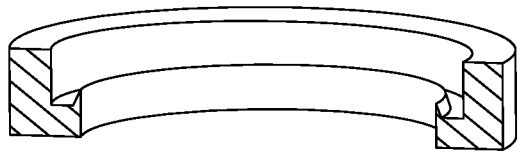
Figure 12:
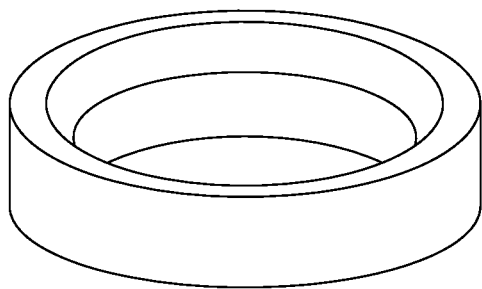
Figure 13:
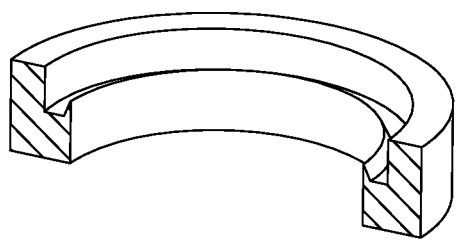
Figure 14:
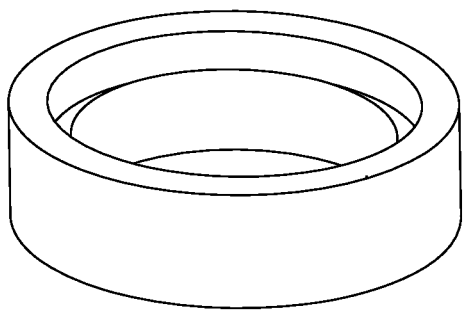
Figure 15:
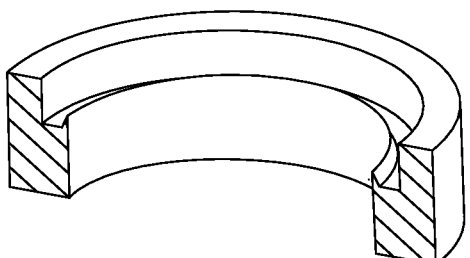
Figure 16:
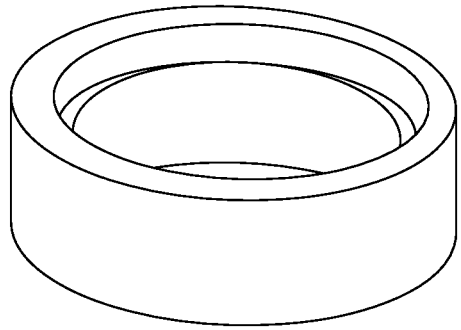
Figure 17:
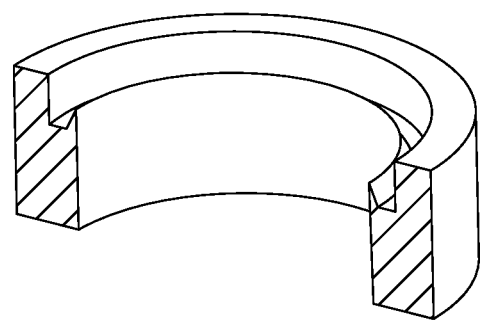
Figure 18:
Figure 19:
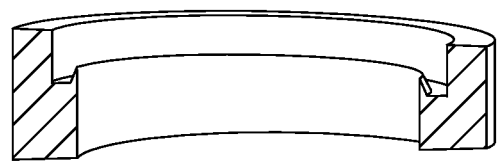
Figure 20:
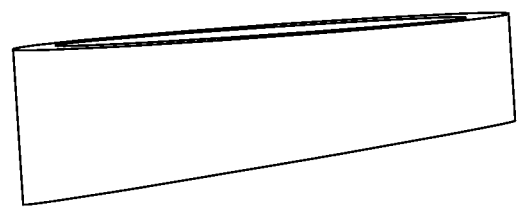
Figure 21:
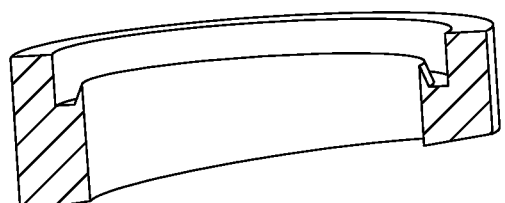
Figure 22:
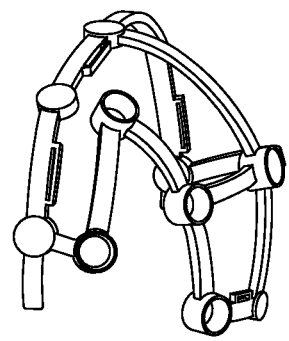
Figure 23:
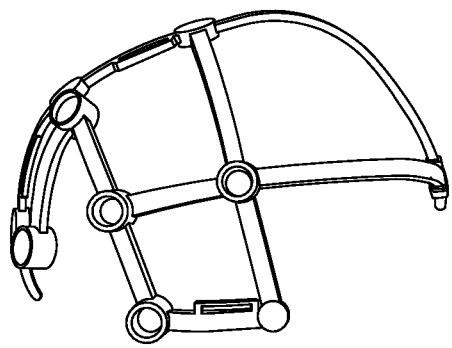
Figure 24:
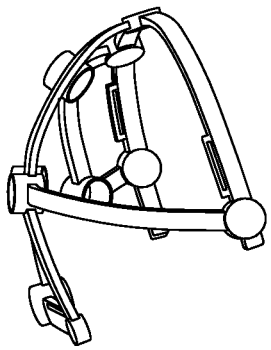
Figure 25:
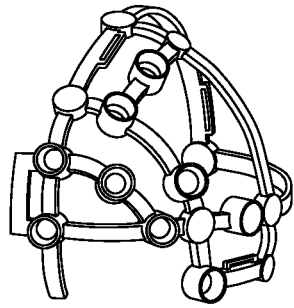
Figure 26:
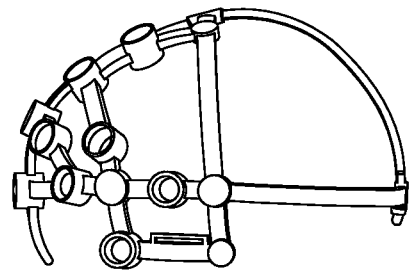
Figure 27:
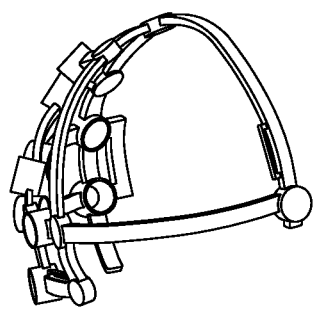
Figure 28:
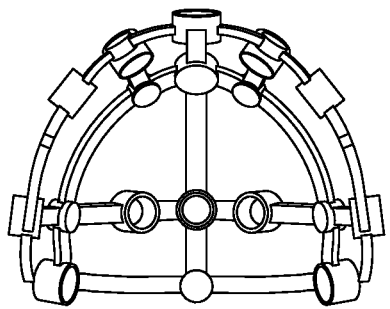
Figure 29:
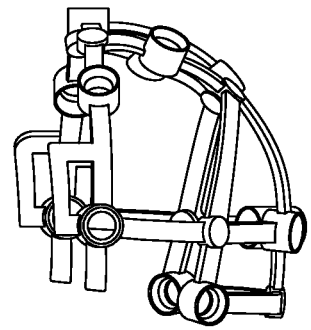
Figure 30:
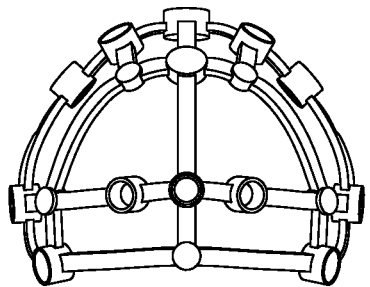
Figure 31:
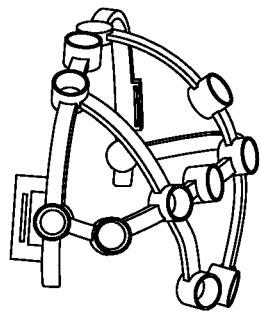
Figure 32:
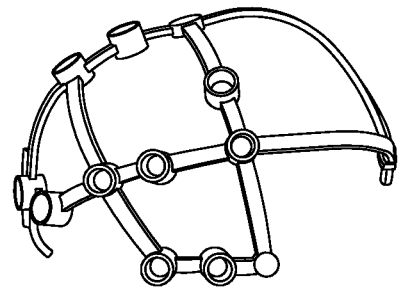
Figure 33:
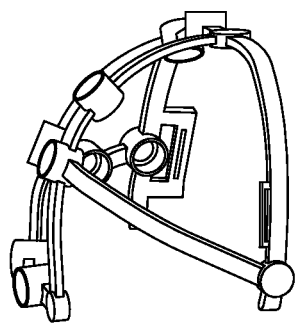
Figure 34:
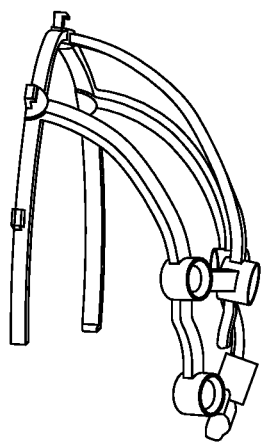
Figure 35:
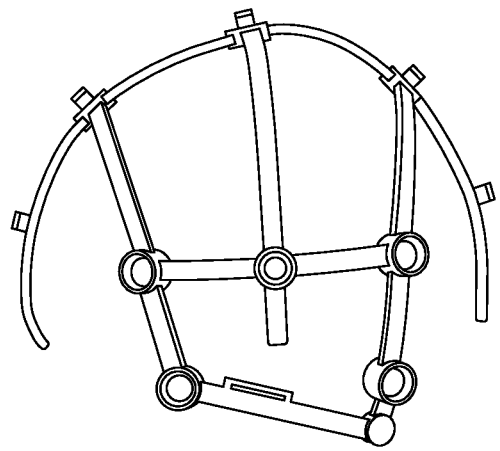
Figure 36:
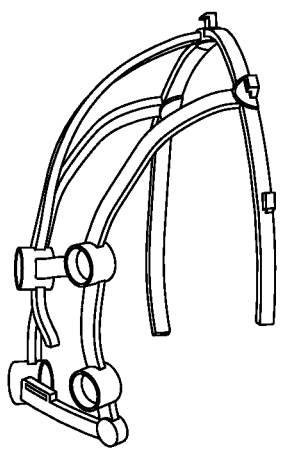
Figure 37:
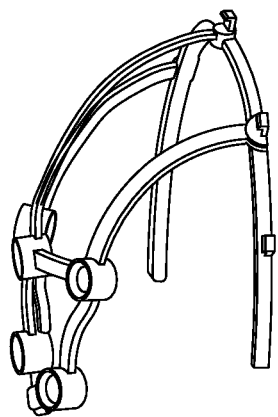
Figure 38:
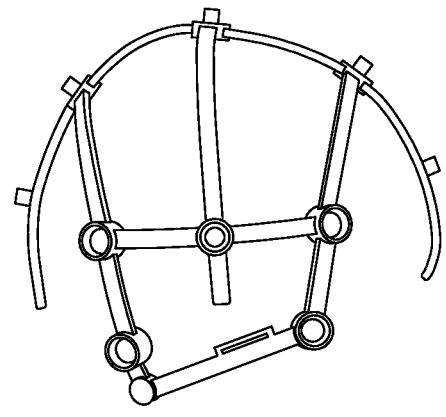
Figure 46:
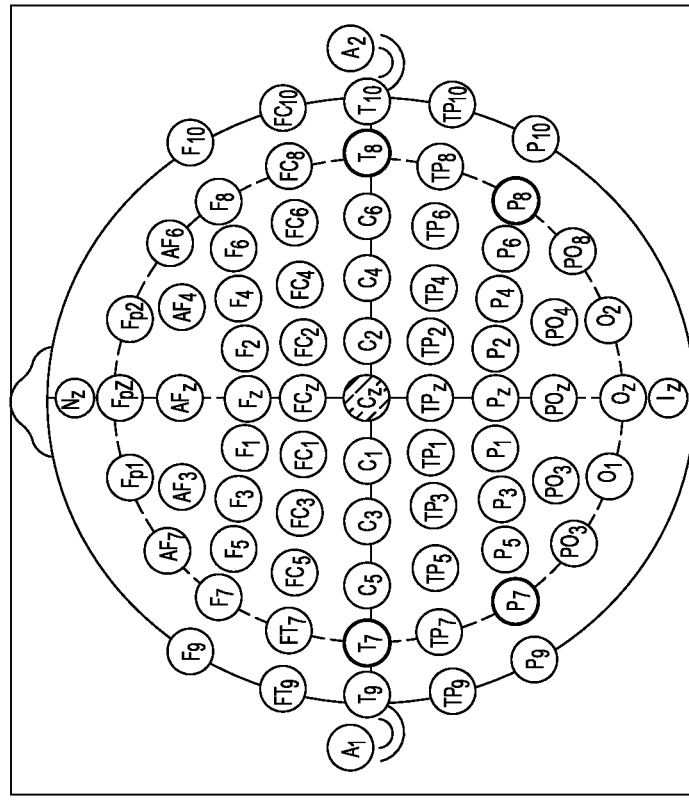
FIG. 46 illustrates selection of anode and cathode locations from the 10/10 system according to the principles of the present teachings.
Figure 47:
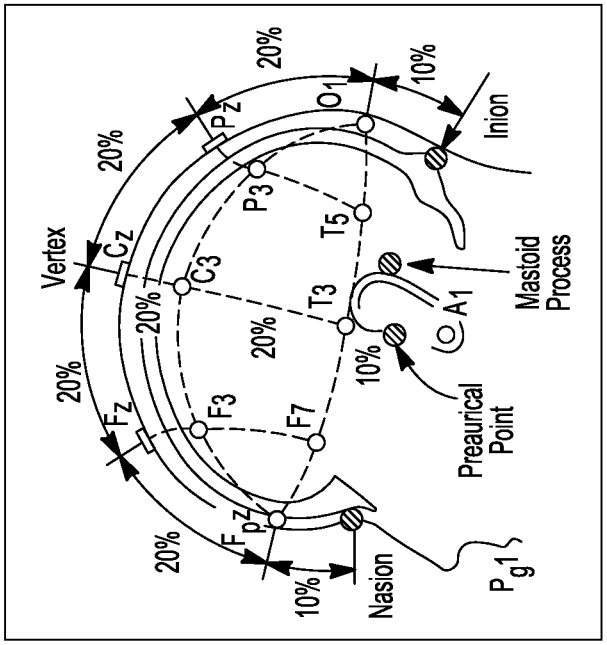
FIG. 47 illustrates an input of patient's landmark measurements and 3D scan according to the principles of the present teachings.
Figure 48:
FIG. 48 illustrates selection of nasion from a 3D scan according to the principles of the present teachings.
Figure 48:
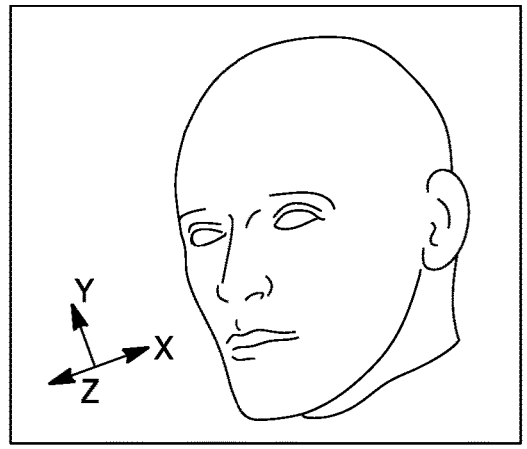
Figure 49:
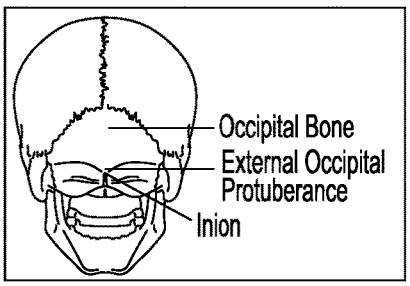
FIG. 49 illustrates selection of inion from a 3D scan according to the principles of the present teachings.
Figure 49:
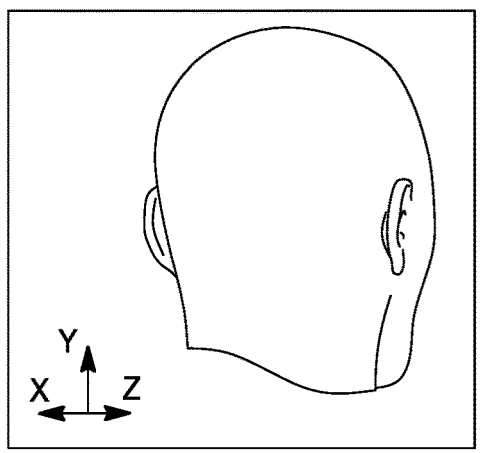
Figure 50:
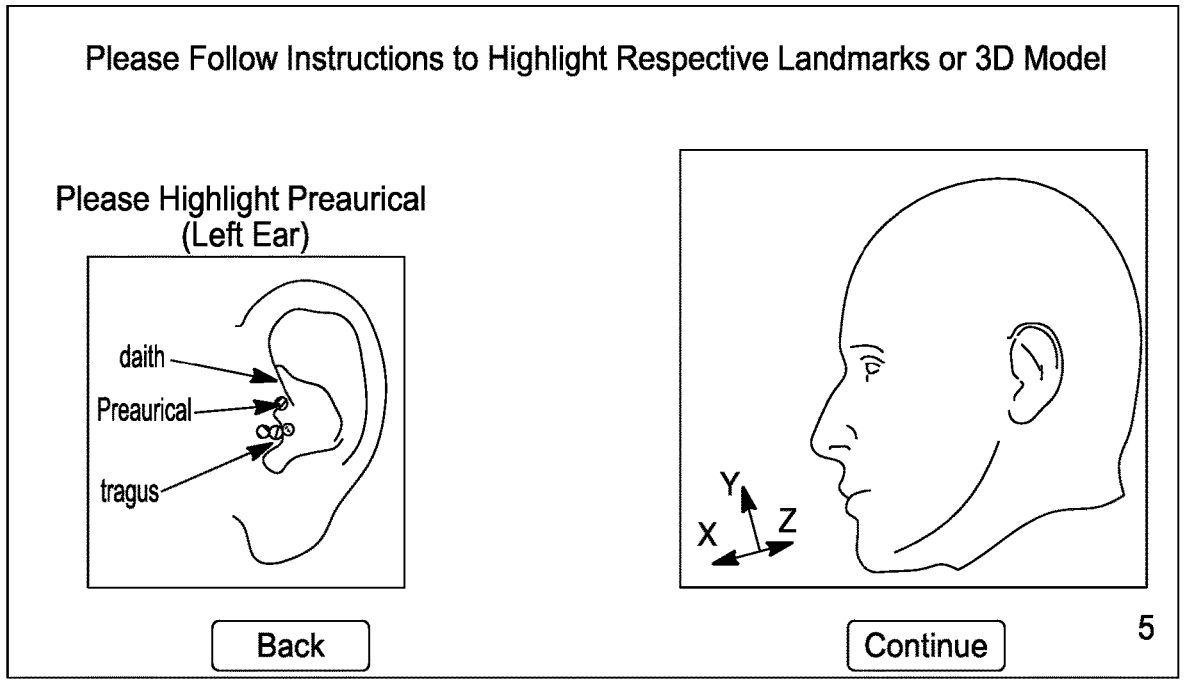
FIG. 50 illustrates selection of left preauricular point from a 3D scan according to the principles of the present teachings.
Figure 51:
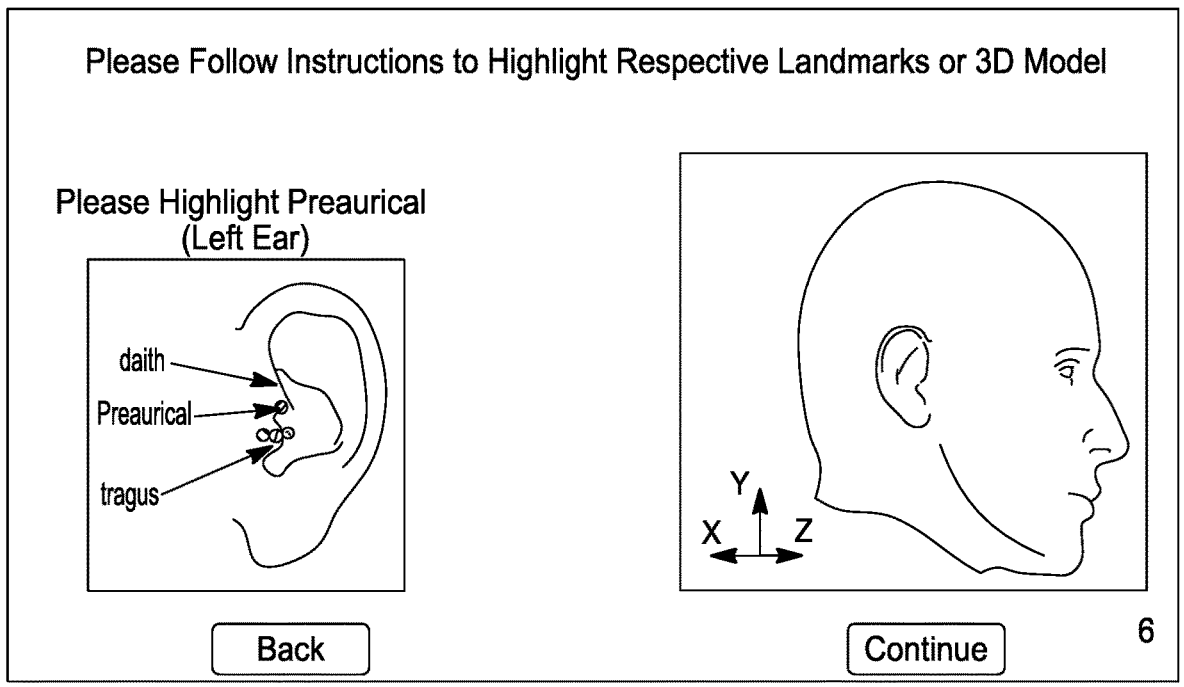
FIG. 51 illustrates selection of right preauricular point from a 3D scan according to the principles of the present teachings.
Figure 52:
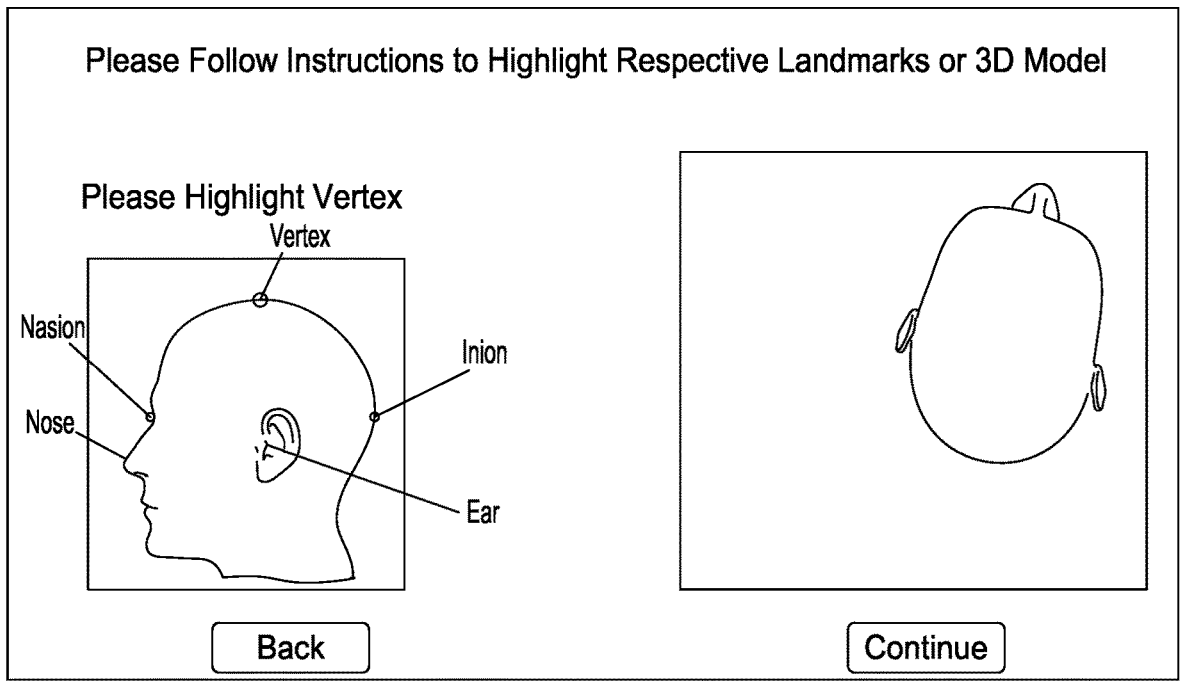
FIG. 52 illustrates selection of vertex point from a 3D scan according to the principles of the present teachings.
Figure 53:
FIG. 53 illustrates the generation of an STL file for a patient's custom apparatus according to the principles of the present teachings.

In some embodiments, as illustrated in FIG. 9, an electrode cap 70 can be selectively coupled to an open end of electrode cup 60 to capture electrode 100 and electrode gel, if used, within electrode cavity 64. In some embodiments, electrode cap 70 comprises a coupling means, such as tabs 72, threads, snap fit features, or the like, for selectively securing electrode cap 70 to electrode cup 60. In some embodiments, a cap standoff surface 74 is provided within an inner surface of electrode cap 70 to contact or otherwise position electrode 100 within electrode cavity 64 by contacting electrode 100 when electrode cap 70 is secured to electrode cup 60. Electrode cap 70 can form a sealing engagement with electrode cup 60 to contain and prevent leakage of electrode gel within electrode cavity 64.

Electrode cup 60 and/or electrode holder 14 maximize the seal formed between electrode cup 60 and/or electrode holder 14 and the scalp for improved performance. In some embodiments, as illustrated in FIGS. 10-21, electrode cup 60 can be manufactured in varying depth sizes and/or angles to enable refined adjustment of electrode 100 relative to the patient. In this way, structural frame 12 does not need to be reprinted or remanufactured in the event electrode contact with a patient needs to be adjusted (i.e. to adjust distance and/or angle between electrode 100 and the patient's head).

In some embodiments, electrode holders 14 and/or electrode cup 60 can be made of the same material as structural frame 12 or other features of headgear assembly 10. However, the material of electrode holders 14 can be different from the material of structural frame 12 to better conform to biologic or electrical properties. In some embodiments, electrode holders 14 and/or electrode cup 60 can be made of flexible material in order to ensure optimal fit. Moreover, in some embodiments, electrode cup 60 can be 3D printed using a Stratasys J750 with "clear" Agilus30 as the material.

In some embodiments, electrode cup 60 can comprise any suitable materials, variations of silicone, including medical grade silicone, along with other rubber-like materials. It should be understood that electrode cup 60 can be mass-produced using any suitable means (i.e. injection molding, etc.) and inserted into electrode holder 14 of customized structural frame 12.

In some embodiments, electrode cup 60 can comprise physical indicators (such as bumps or various designs (e.g., shapes, numbers, colors, or similar distinguishing features)) to differentiate the various sizes and fits. In some embodiments, electrode cup 60 can be tailored to all various sizes and types of electrodes that exist or may come into existence in order to expand the utility of the primary headgear device with other electrode systems, such as electrodes that require close or direct contact with the skin, including dry electrodes.

In some embodiments, as illustrated in FIG. 7, a label 50 can be disposed adjacent to a corresponding electrode holder 14 on crossbar rib member 22 and/or interconnecting support member 24 to identify the proper location of a particular electrode 100. This can aid a user in properly configuring headgear assembly 10 for use and ensure proper application of treatment or monitoring.

Example Accuracy Data

The use of 2-3 landmark locations ensures that, when appropriately aligned, the holder locations will be in the same location from session to session. A series of tests was performed on actual participants in which the location of electrodes was compared, on two separate days, based on a) measurements from different trained staff members relative to b) those from the individually tailored headgear. It should be noted that, because the headgear is rigid and, therefore, cannot vary the holder location, any error arises from human measurement. Importantly, these values were within ~3-5 mm of the human based measures. Thus, the goal of creating an individualized and accurate method of HD-tDCS was achieved.

Example Precision Data

The electrode location was compared between that of headgear assembly 10 to the same ostensible location identified by the Soterix Medical Inc., neoprene head cap for PT1 (using a 58 cm circumference head cap) vs. a 10-electrode version of headgear assembly 10 (having several locations from the 10/5 system). The landmark positions noted on the neoprene head cap were markedly inaccurate but were aligned as closely as possible. Of the 5 locations that could be directly compared between headgear assembly 10 and the neoprene cap, there was an average difference of 22 mm (SD=5.15 mm). Headgear placement was also compared using a staff member who did not have any direct experience using the headgear and found highly accurate placement (average difference=0.9 mm; SD=1.1 mm). Finally, measurements were compared for a highly experienced and trained staff member placing headgear assembly 10 versus a patient's spouse placing it (without any prior training), which resulted in an average difference of 4.4 mm (SD=1.71 mm).

In another set of experiments, patients' spouses/family (or other trusted individuals) were briefly trained to administer HD-tDCS using headgear assembly 10 in order to perform remotely supervised HD-tDCS via videoconference. To this end, training procedures were developed, tested, and refined to facilitate the spouse/family/other member's ability to place headgear assembly 10, fill the electrode holders 14, place the electrodes 100 and secure headgear assembly 10, and operate the stimulator. Data are present in Table 1 from spouses of two patients, both of whom completed approximately 15 minutes of training before being asked to place the headgear. As seen, placement was highly accurate and well within a targeted range of <10 mm.

TABLE 1

|  | Session 1 | Session 2 | Session 3 |
| --- | --- | --- | --- |
| Spouse 1 - Headgear with 5 electrodes | 0.4 mm | 1.0 mm | 0.6 mm |
| Spouse 2 - headgear with 10 electrodes | 2.2 mm | 3.0 mm |  |

These difference values are especially impressive given prior work that utilized a custom NeuroMedical cap to test variability of electrode locations across participants and sessions, which found that standard deviations ranged from 3.0 to 12.7 mm.

In summary, headgear assembly 10 resulted in highly consistent electrode placement, across staff members, patients, days, and montages. Additionally, headgear assembly 10 was far more accurate than conventional designs. Finally, untrained/nominally trained spouses placed headgear assembly 10 within an acceptable level of accuracy.

Software

In some embodiments, as illustrated in FIGS. 46-54, in order to ensure ease of use and rapid headgear development, software has been created to guide the user through the necessary measurements, selecting the desired electrode montage (locations), and marking important landmarks on the 3D model. The software then utilizes this information to procedurally develop the 3D CAD file for a customized device. In some embodiments, any one or a combination of data entry can be used, such as but not limited to: 1) manual entry of key distances relative to landmarks, 2) measurements taken from magnetic resonance imaging (MRI) scans, which provide a detailed, 3D outline of the head, and 3) 3D scans of the patient's head. Additional forms of data entry can be integrated as appropriate to ensure the most accurate headgear fit possible. From this inputted information, the software outputs an STL file of the headgear to be printed for the patient.

Figure 54:
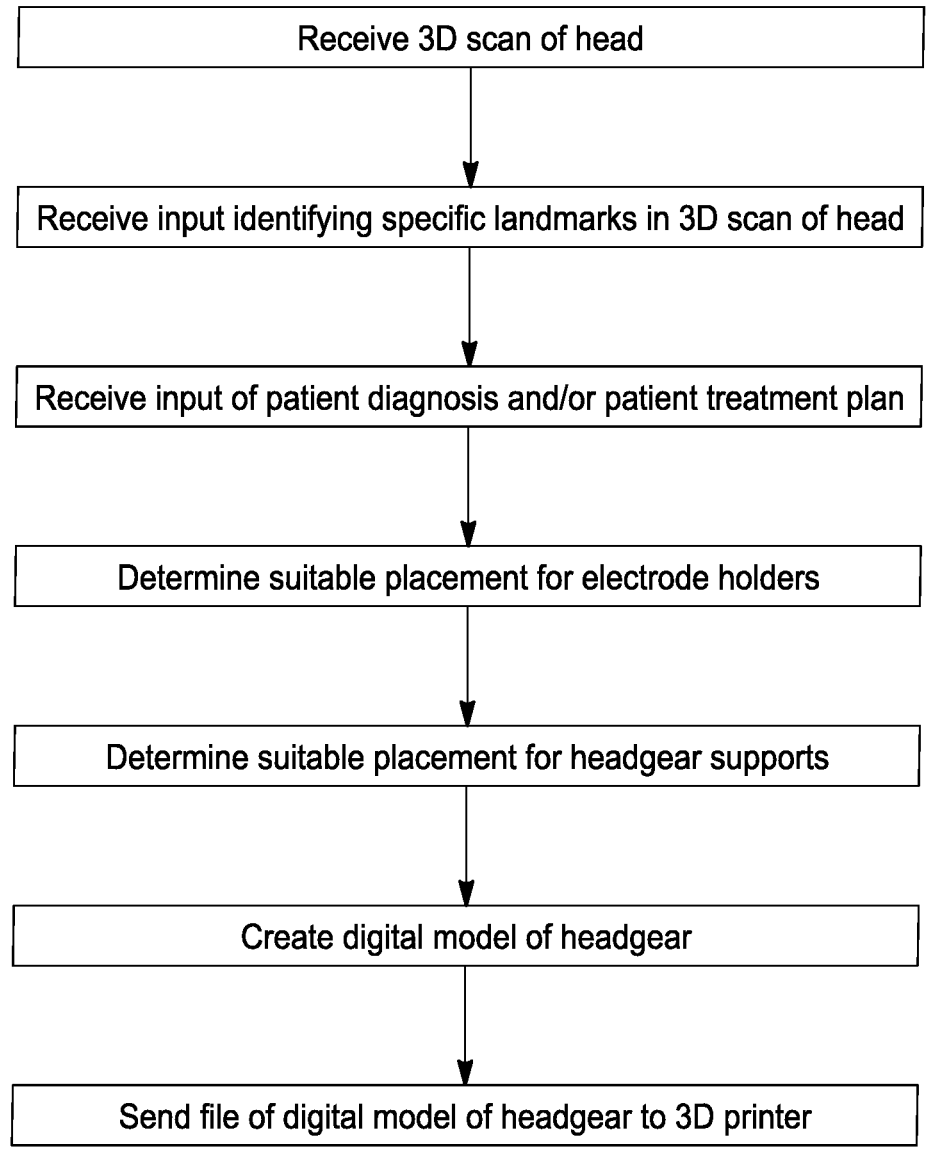
FIG. 54 illustrates a flow chart of one example of a method of designing and manufacturing a custom headgear apparatus according to the principles of the present teachings.

As shown in the flow chart provided in FIG. 54, in at least some embodiments, a custom headgear apparatus of the present teachings is designed and manufactured semi-automatically with the assistance of the software. A computer running the software program receives as an input a 3D scan of the head. In some embodiments, the 3D scan is from an MRI baseline scan. In some such embodiments, the file type generated by the MRI (e.g., a NIfI-1 file) is converted to a file type that is readable and editable by the software program (e.g., an STL file). In other embodiments, the 3D scan is generated from an image (e.g., a photographic image) of the head obtained using readily available tools, such as but not limited to smartphone or tablet cameras and/or associated devices or peripherals. The 3D scan is rendered on a display screen. The software program of some embodiments prompts a user to identify specific common landmarks in the displayed 3D scan, which the user can do, for example, with a mouse click over the requested landmark. The user may be prompted to identify one or more of the nasion, inion, preauricular points, or other meaningful landmarks. In other embodiments, the software program is able to automatically identify these landmarks (e.g., via machine learning) and may request confirmation of accuracy from the user. In various embodiments, the program may also prompt a user to input a patient treatment plan (e.g., the 10/10 or 10/5+ System or other desired treatment or monitoring plan). Alternatively, the program may prompt a user to input a patient diagnosis, and the program may be configured to identify a recommended treatment or monitoring plan based on the diagnosis. Based on the inputs of the 3D scan, the specific landmarks, and the patient treatment plan and/or diagnosis, the program determines a proper placement for electrode holders and a proper placement for headgear supports to hold the electrode holders in the proper position/alignment. Based on the identification of a proper placement for the electrode holders and headgear supports, the program of various embodiments creates a digital model of the headgear apparatus. This digital model is rendered in a file type readable by a 3D printer. The file may then be sent to a 3D printer for printing/manufacturing, for example, upon receiving an input to print from a user.

Exemplary headgear assemblies 10 according to the principles of the present teachings are illustrated in FIGS. 22-45.

Example Standard Operating Procedures

By way of reference, the following represents standard operating procedures for set, pre-session, during session, and post-session:

Standard Operating Procedures upon Receiving Headgear Print Confirmation & Setup
1. Visually inspect device to confirm the montage is correct and electrode holders/landmarks are logically placed and in line with expectations.
2. Check all support material has been removed from the device. Remaining support material can be removed using fingers, paperclips, sanding, and other similar methods.
3. Test each electrode holder with a cap making sure it twists into position and can be removed without being stuck.
4. If printed in two halves, rubber band at least the middle connective posts in order to ensure the headgear stays together, but keeps the flexibility required to place the device on the participant's head.
5. Thread chinstrap through one of the loops with the Velcro side facing the support bar. Once entire strap is pulled through, fold strap loop over support bar, so it is parallel to the loop on the headgear.
6. Thread strap back through loop on the strap pulling all the way through making sure the Velcro side is facing out.
7. Pull strap through the other loop on the helmet from the inside of the helmet towards the outside.
8. Fold strap over support bar so Velcro clings to itself.

Pre-Session
1. Retrieve the headgear from its storage place and ensure the identification label matches the individual.
2. Before placing the headgear on the participant's head, unstick Velcro from itself and loosen it sufficiently to be fitted on the participant's head.
3. Place the helmet on the participant's head with the label facing forward using the nasion, inion, preauricular, and Cz reference points (and/or other landmarks as available) to correctly align the headgear.
4. If connective pieces are present, rubber band together as many as required to keep the headgear securely together.
5. Place the strap in the proper orientation, and ask the participant to tighten the strap so it is comfortable while still keeping the headgear secure.
6. Once again, make sure all the landmarks are correctly aligned and the electrode locations align with desired locations.
7. For the first fitting, check each electrode holder location to see how far (if at all) the holder is away from the scalp.
8. If the holder does not contact the scalp/skin, fit the holder with an appropriately sized gel cup so the gel cup is in contact with the scalp/skin.
9. Note the location and size of the gel cup for future reference.
10. Note the location and size of the gel cup for future reference.
11. Once fitted with electrode cups (as needed), remove/reposition hair from under the electrode holder to ensure a clear line of sight through the holder to the scalp/skin. Fill electrode holders with gel up to the pegs where the electrode will sit within the holder. Ensure there are no bubbles or gaps in the gel as this will prevent or alter the flow of the electric current.
12. Place an electrode in each holder, threading the wire through the wire notch before plugging it into the appropriate adapter.
13. Fill each holder with the remaining volume with gel.
14. Place the caps on twisting them to the right to make sure they are securely placed.
15. Test the impedance and ensure location has appropriate values, making appropriate adjustments if values exceed acceptable limits.

During Session
16. Supply desired treatment making sure to monitor that the headgear does not shift around or move locations throughout the treatment.

Post Session
17. Once the session is complete, loosen the strap, and remove the headgear.
18. Place it on paper towels, so the gel does not leak onto the floor.
19. Remove the caps, electrodes, and electrode cups from each holder placing them on a paper towel so they may be cleaned.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A customizable headgear assembly for neuropsychological and neurological treatment, monitoring, or testing of a patient, the headgear assembly comprising:
a structural frame individually tailored and manufactured for the patient having at least one anatomical landmark tab, a position of the at least one anatomical landmark tab being located upon an individually tailored anatomical landmark of the patient's head and the at least one anatomical landmark tab coinciding with the individually tailored anatomical landmark of the patient's head, the structural frame having first and second portions releasably coupled to enable the first and second portions to be at least partially separated for placement and removal from the patient's head; and a plurality of electrode holders operably coupled to the structural frame, the plurality of electrode holders each configured to locate an electrode upon an individually tailored neurological position of the patient.

2. The customizable headgear assembly according to claim 1 wherein the at least one anatomical landmark tab comprises a plurality of anatomical landmark tabs configured to be positioned adjacent at least the nasion, inion, and the preauricular points of the individual patient's head.

3. The customizable headgear assembly according to claim 1 wherein the structural frame is non-pliable.

4. The customizable headgear assembly according to claim 1 wherein the structural frame comprises a plurality of paired connector posts, a first of the paired connector posts extending from the first portion of the structural frame and a second of the paired connector posts extending from the second portion of the structural frame, the first connector post and the second connector post being releasably coupled.

5. The customizable headgear assembly according to claim 4 wherein the first connector post and the second connector post are aligned to be releasably coupled.

6. The customizable headgear assembly according to claim 4 wherein the first connector post and the second connector post are releasably coupled using a retaining member.

7. The customizable headgear assembly according to claim 6 wherein the retaining member comprises a clip or clamp.

8. The customizable headgear assembly according to claim 6 wherein the retaining member comprises a mechanical interconnection.

9. The customizable headgear assembly according to claim 6 wherein the retaining member comprises an elastic member.

10. The customizable headgear assembly according to claim 6 wherein the retaining member is compliant.

11. The customizable headgear assembly according to claim 1 wherein the structural frame comprises a plurality of crossbar rib members extending from a central spine member, at least one of the plurality of electrode holders being operably coupled to at least one of the plurality of crossbar rib members.

12. The customizable headgear assembly according to claim 11 wherein the structural frame comprises an interconnecting support member operably coupled to at least one of the plurality of crossbar rib members.

13. The customizable headgear assembly according to claim 11 wherein the structural frame comprises an interconnecting support member operably coupled to the least one of the plurality of electrode holders.

14. The customizable headgear assembly according to claim 1, further comprising:

a plurality of electrode cups each operably coupled to a corresponding one of the plurality of electrode holders, each of the plurality of electrode cups being sized and configured to contact the patient's head, each of the plurality of electrode cups having a cavity configured to receive the electrode.

15. The customizable headgear assembly according to claim 14, further comprising:

a plurality of electrode caps each being coupled to a corresponding one of the plurality of electrode cups, each of the plurality of electrode caps retaining the electrode within the electrode cavity of the corresponding one of the plurality of electrode cups.

16. The customizable headgear assembly according to claim 1, formed by a method comprising:

determining an individually tailored anatomical landmark map of the patient's head;

determining a placement location of the electrode based upon the individually tailored anatomical landmark map of the patient's head and collocating a corresponding one of the plurality of electrode holders at the individually tailored neurological position to locate the electrode thereat;

determining a structural frame orientation to support the plurality of electrode holders; and constructing the structural frame and the plurality of electrode holders to manufacture the customizable headgear assembly for the individual patient.

17. The method according to claim 16 wherein the determining an anatomical landmark map of the patient's head comprises scanning the patient's head using a scanning device.

18. The method according to claim 17 wherein the scanning device is a magnetic resonance imaging machine.

* * * * *

UNITED STATES PATENT AND TRADEMARK OFFICE
CERTIFICATE OF CORRECTION

| | |
|---|---|
| PATENT NO. | : 11,865,328 B2 |
| APPLICATION NO. | : 17/188437 |
| DATED | : January 9, 2024 |
| INVENTOR(S) | : Benjamin Hampstead et al. |

It is certified that error appears in the above-identified patent and that said Letters Patent is hereby corrected as shown below:

On the Title Page

Column 1, (71) Applicant, Line number 3, delete "(US)" and insert --(US); The United States Government as represented by the Department of Veterans Affairs, Washington, DC (US)--.

Signed and Sealed this
Fifth Day of March, 2024

Katherine Kelly Vidal
*Director of the United States Patent and Trademark Office*